United States Patent
Swennen et al.

(10) Patent No.: US 11,147,600 B2
(45) Date of Patent: Oct. 19, 2021

(54) BONE IMPLANT FOR THE RECONSTRUCTION OF AN OSSEOUS DEFECT AND FOR GUIDING A MARKING AND/OR PROCESSING TOOL FOR TRANSFERRING REQUIRED OSTEOTOMY SITUATIONS

(71) Applicant: KARL LEIBINGER MEDIZINTECHNIK GMBH & CO. KG, Mühlheim (DE)

(72) Inventors: Gwen Swennen, Knokke (DE); Adem Aksu, Villingen-Schwenningen (DE); Frank Reinauer, Emmingen-Liptingen (DE); Heiner Wild, Dürbheim (DE)

(73) Assignee: KARL LEIBINGER MEDIZINTECHNIK GMBH & CO., Muhlheim (DE)

(*) Notice: Subject to any disclaimer, the term of this patent is extended or adjusted under 35 U.S.C. 154(b) by 188 days.

(21) Appl. No.: 16/555,046

(22) Filed: Aug. 29, 2019

(65) Prior Publication Data
US 2020/0069427 A1 Mar. 5, 2020

(30) Foreign Application Priority Data
Sep. 4, 2018 (DE) .................. 10 2018 121553.3

(51) Int. Cl.
*A61B 17/80* (2006.01)
*A61F 2/28* (2006.01)
(Continued)

(52) U.S. Cl.
CPC .......... *A61B 17/8061* (2013.01); *A61B 17/15* (2013.01); *A61B 17/1739* (2013.01); *A61F 2/2875* (2013.01); *A61B 17/1695* (2013.01)

(58) Field of Classification Search
CPC ... A61F 2/2875; A61B 17/80; A61B 17/8052; A61B 17/8057; A61B 17/8061; A61B 17/8085
(Continued)

(56) References Cited

U.S. PATENT DOCUMENTS 5,201,737 A * 4/1993 Leibinger ............ A61B 17/688
606/280
5,468,242 A * 11/1995 Reisberg ............ A61B 17/8085
606/151
(Continued)

FOREIGN PATENT DOCUMENTS

CA        3 019 738 A1     11/2017
DE    102016108433 A1     11/2017
(Continued)

OTHER PUBLICATIONS

German Search Report for DE 10 2018 121 553.3, dated Aug. 1, 2019 (in German) (8 pp.).
(Continued)

*Primary Examiner* — Eric S Gibson
(74) *Attorney, Agent, or Firm* — Eversheds Sutherland (US) LLP (57) ABSTRACT

The invention relates to a bone implant for attaching to on a surface of a bone, including a base body whose lower side and/or upper side correspond(s) substantially to a deformation-free bone outer contour, wherein the outer dimensions of the base body are chosen such that the base body covers a specifically introduced deformation region for obtaining autologous bone material completely, wherein in the base body at least one slot is provided which is dimensioned such that it guides a bone marking and/or bone processing tool inserted in the slot in use.

9 Claims, 5 Drawing Sheets

(51) Int. Cl.
*A61B 17/17* (2006.01)
*A61B 17/15* (2006.01)
*A61B 17/16* (2006.01)

(58) Field of Classification Search
USPC .......................................................... 606/903
See application file for complete search history.

(56) References Cited

U.S. PATENT DOCUMENTS

| | | | | |
|---|---|---|---|---|
| 5,743,913 | A * | 4/1998 | Wellisz | A61B 17/8061 |
| | | | | 606/285 |
| 5,752,958 | A * | 5/1998 | Wellisz | A61B 17/8085 |
| | | | | 606/280 |
| 5,766,176 | A * | 6/1998 | Duncan | A61B 17/8085 |
| | | | | 606/281 |
| 5,814,048 | A * | 9/1998 | Morgan | A61B 17/8085 |
| | | | | 606/283 |
| 5,980,540 | A * | 11/1999 | Bruce | A61B 17/8085 |
| | | | | 606/151 |
| 6,071,291 | A * | 6/2000 | Forst | A61B 17/8085 |
| | | | | 606/151 |
| 6,942,665 | B2 * | 9/2005 | Gambale | A61F 2/2846 |
| | | | | 606/285 |
| 9,220,597 | B2 * | 12/2015 | Engstrand | A61F 2/2875 |
| D751,202 | S * | 3/2016 | Gabele | A61B 17/8061 |
| | | | | D24/155 |
| 9,517,097 | B2 * | 12/2016 | Rise et al. | A61B 17/8085 |
| 9,549,819 | B1 * | 1/2017 | Bravo | A61B 17/8085 |
| 9,744,042 | B2 * | 8/2017 | Beerens | A61B 17/17 |
| 10,076,416 | B2 * | 9/2018 | Engstrand | A61F 2/28 |
| 10,111,752 | B2 * | 10/2018 | Howard | A61B 17/8061 |
| 10,881,519 | B2 * | 1/2021 | Engstrand | A61F 2/2875 |
| 2005/0149032 | A1 * | 7/2005 | Vaughen et al. | A61B 17/8085 |
| | | | | 606/77 |
| 2005/0261780 | A1 * | 11/2005 | Heino | A61B 17/8085 |
| | | | | 623/23.51 |
| 2005/0288790 | A1 * | 12/2005 | Swords | A61F 2/2875 |
| | | | | 623/17.19 |
| 2006/0224242 | A1 * | 10/2006 | Swords | A61B 17/8085 |
| | | | | 623/17.19 |
| 2008/0009872 | A1 * | 1/2008 | Vaughen et al. | A61B 17/8085 |
| | | | | 606/71 |
| 2012/0203289 | A1 * | 8/2012 | Beerens | A61B 17/17 |
| | | | | 606/323 |
| 2014/0228969 | A1 * | 8/2014 | Engstrand | A61B 17/688 |
| | | | | 623/23.47 |
| 2014/0316472 | A1 * | 10/2014 | Rise et al. | A61B 17/8085 |
| | | | | 606/281 |
| 2015/0105806 | A1 * | 4/2015 | Dorafshr | A61L 31/146 |
| | | | | 606/151 |
| 2015/0374497 | A1 * | 12/2015 | Engstrand | A61B 17/688 |
| | | | | 623/17.19 |
| 2017/0239054 | A1 * | 8/2017 | Engstrand | A61B 17/688 |
| 2017/0273794 | A1 * | 9/2017 | Howard | A61F 2/2875 |
| 2018/0271657 | A1 * | 9/2018 | Mizukami | A61F 2/2875 |
| 2020/0069427 | A1 * | 3/2020 | Swennen | A61B 17/15 |
| 2020/0315803 | A1 * | 10/2020 | Zille | A61F 2/2803 |
| 2020/0360058 | A1 * | 11/2020 | Garcia | A61B 17/8061 |

FOREIGN PATENT DOCUMENTS

| | | | | |
|---|---|---|---|---|
| EP | 3 000 439 A1 | | 3/2016 | |
| JP | 11155879 A | * | 6/1999 | ......... A61B 17/8085 |
| JP | 2000135230 A | * | 5/2000 | ......... A61B 17/8061 |

OTHER PUBLICATIONS

German Search Report for DE 10 2018 121 553.3, dated Aug. 1, 2019 (in English) (7 pp.).

* cited by examiner

BONE IMPLANT FOR THE RECONSTRUCTION OF AN OSSEOUS DEFECT AND FOR GUIDING A MARKING AND/OR PROCESSING TOOL FOR TRANSFERRING REQUIRED OSTEOTOMY SITUATIONS

TECHNICAL FIELD

The invention relates to a bone implant for the reconstruction and/or restitution of an osseous (osteotomy) situation and for attaching to a surface of a bone, in particular a cranial bone.

BACKGROUND OF THE INVENTION

From the state of the art bone implants are already known for the filling and/or closing a defect and/or for the repositioning in the cranial bone. DE 20 2014 103 858 U1, for instance, discloses an implant for the repositioning and fixation of a centro-lateral midfacial fracture, wherein the implant comprises a plurality of preformed segments, preferably three or more preformed segments, wherein the shape of a first segment is designed such that at least its lower side resting on the bone is completely or partially complementary to the anatomic structure of at least a partial area of the outer side of an upper jaw bone, wherein the shape of the second segment is designed such that at least its lower side resting on the bone is completely or partially complementary to the outer anatomic structure of a web region between the upper jaw and the cheekbone, and wherein the shape of a third segment is designed such that at least its lower side resting on the bone is completely or partially complementary to the anatomic structure of at least an outer partial area of a cheekbone.

Also, devices for the guiding of sectioning tools are already known from the state of the art. DE 10 2015 107 484 A1, for instance, discloses a bone connecting implant for connecting a first bone region with a second bone region or a plurality of bone regions of a mammalian bone with a first fastening region comprising a plurality of fastening means receiving holes and prepared for being attached to a first bone region, and a second fastening region connected with the first fastening region, wherein the second fastening region in turn comprises a plurality of fastening means receiving holes and is prepared for attached to on the second bone region, wherein a sectioning tool guiding contour defining a sectioning line is formed between the first and second fastening regions.

It is thus known to use, for correcting a bone malposition, a bone implant which is individually adapted to the corrected bone malposition and corresponds to a correct position, so that correcting is facilitated. It is also known to use a bone implant so as to form contours on the bone implant for correcting a malposition, said contours guiding a sectioning tool to enable the simple forming of a defined sectioning contour. However, no solution is known from the state of the art by means of which autologous bone material, for instance, from the cranial bone, can be obtained with relatively little effort and minor effects on the patient from a non-malpositioned bone region so as to transplant the bone material to another position of the body to remedy a defect there.

SUMMARY OF THE INVENTION

It is thus an object of the invention to avoid or at least reduce the disadvantages of the state of the art. In particular, a bone implant is to be provided which assists the removal of autologous bone material from a non-deformed/non-malpositioned region, so that a necessary operation time for removal may be kept as short as possible and no negative effects thus occur for the patient.

The object of the invention is solved in accordance with the invention by a bone implant for attaching to a surface of a bone, for instance, a cranial bone, wherein the bone implant comprises a base body whose lower side and/or upper side corresponds substantially to a deformation-free bone outer contour, for instance, a deformation-free cranial outer contour, wherein the outer dimensions are chosen such that the base body covers a specifically introduced deformation region for obtaining autologous bone material completely, wherein at least one slot is provided in the base body, said slot being dimensioned such that it guides a bone marking and/or bone processing tool inserted in the slot in use. This means thus that the bone implant, in particular the base body of the bone implant, corresponds to a surface contour and/or a surficial bone layer in a defect-free, i.e. non-malpositioned, region. The bone implant is hence not used to correct a (natural) defect or a malposition, but to replace a natural region without modifying the form thereof. In other words, the invented bone implant corresponds to a superficial bone layer or bone plate of the skull area where it is inserted. Thus, the skull area where the bone implant is inserted is deformation-free before insertion and after insertion. This means that the skull area where the bone implant is inserted is geometrically not changed, or only changed as slightly as possible, by the implantation of the bone implant.

A deformation means a (depression-like) malposition as compared to the adjacent surface region of the cranial bone, for instance, caused by a specifically formed, i.e. desired, bone removal. This means, artificially formed/applied so as to obtain bone material.

The base body comprises the slot which serves as a marking and/or sectioning tool guiding contour for forming/applying the deformation/the depression. This has the advantage that, due to the predefining of the sectioning lines through the base body, the sectioning lines correspond to the form of the base body, so that the artificial defect/the deformation/the depression may be covered and/or closed again in a precisely fitting manner by the base body. Thus, the artificial defect for the removal of bone is not visible, so that the effect on the patient is hardly perceptible. Moreover, the operation time may be shortened considerably by the guided forming/inserting/making of the sectioning lines.

Advantageous embodiments are claimed in the subclaims and will be explained in detail in the following.

Moreover, it is expedient if the bone implant serves as a guide for a sawing tool, so that saw cuts may be applied/made/formed when the bone implant lies on the cranial bone. It is also preferred if the cranial bone is scored, i.e. scratched surficially.

It is preferred if the slot is designed as an elongate through hole enabling the reaching through of the bone marking and/or bone processing tool, in the following called tool, from the upper side of the base body through the material of the base body and beyond the lower side of the base body. The tool may thus reach through the base body to produce a marking and/or sectioning line in sections formed by the slots. This means thus that the position of the marking and/or sectioning lines is predetermined by the arrangement of the slots.

It is also of advantage if a plurality of slots are available, at least two of them being arranged orthogonally to each other. This way a plurality of segments may be formed and/or marked within the region covered by the base body. It is particularly preferred if the slots predefine a pattern, for instance, a checkered pattern with rectangular and/or square and/or triangular segments, wherein the shape of the segments corresponds to a required bone plate shape (for transplantation to the required position). This means thus that the slots confine defined shapes.

It is further expedient if the outer contour of the base body is designed as a guiding face for the bone marking and/or bone processing tool. This means that the tool is guided along both in the slots within the base body and at the outer edges of the base body so as to predefine the sectioning lines and/or marking lines. It is thus ensured that the base body covers the deformation region completely since bone material is merely removed within the outer contour of the base body.

It is particularly advantageous if slot rims, i.e. edges/rims/side faces of the slot or the slots, respectively and/or the lateral edges of the outer contour of the base body are designed to be sloped/inclined toward the upper side and/or the lower side of the base body. This way, engaging of the tool is not performed perpendicularly to the surface of the cranium, but at an angle. This assists the removal of the bone material, for instance, by a chisel.

The slot rims and/or the lateral edges may, for instance, be inclined between 30 and 60°, in particular by 45°±3°. Preferably, the lateral edges are inclined such that they are inclined inwards from the upper side of the base body to the lower side of the base body, i.e. toward the middle of the base body. This means thus that the upper side of the base body is, due to the inclined lateral edges, slightly larger than the lower side of the base body. Preferably, the slot rims are inclined from the upper side of the base body to a middle of the respective segment they confine, and to the lower side.

In accordance with an advantageous further development the lower side of the base body is shaped concavely. Additionally, it may be avoided by the predefinition of defined contact points that the bone implant projects from the surface of the cranial bone due to unevenness in the deformation region. Thus, a particularly smooth transition between the bone implant and the cranial bone is ensured.

Preferably, a marking, preferably an arrow/direction marking, may be provided on the upper side of the base body, said marking indicating an implantation direction. This assists a surgeon advantageously when positioning and/or aligning the bone implant on the cranial bone.

It is also expedient if the bone implant is designed as a generatively produced component. Thus, the shape of the bone implant can be adapted in a particularly simple manner to the individual cranial shape, so that a particularly precisely fitting implant with respect to curvature/bending is produced.

The bone implant, in particular the base body, may, for instance, be produced with an additive method. This has the advantage that an implant which corresponds to the CAD data which are, for instance, produced by optical image processing and which correspond to the shape of the cranial bone may be produced in a simple and cost-efficient manner. Thus, an individual bone implant may be generated.

It is particularly preferred if the bone implant, in particular the base body, has a net-like and/or lattice-like structure. This supports an ingrowing and/or a resorption of the bone implant.

It is further expedient if the base body contains a doping, for instance, of silver and/or only its surface contains particles. The adding of particles may achieve an antimicrobacterial effect, so that the danger of inflammation is reduced.

It is also of advantage if a plurality of slots are separated/interrupted in alignment with each other by (full) material of the base body. Thus, the bone implant has, despite the forming of the slots, sufficiently high stability. At the same time, the marking and/or sectioning lines may be made through the slots into the cranial bone to such an extent that they can be completed easily.

It is further preferred if the bone implant comprises fastening lugs projecting outwardly from the base body, for instance, like ears. It is thus possible to fasten the bone implant on the cranial bone, for instance, by screwing. This may be used at the time of making/inserting/forming the sectioning and/or marking lines and/or for the permanent fastening in the cranial bone during the covering of the deformation region. It is also possible that the bone implant is used without a fastening device since, due to the precisely fitting shape, a positive-locking resting is sufficient to determine a position of the bone implant.

In a preferred embodiment the base body may have a constant thickness. Preferably, the fastening lugs also have a constant thickness. Thus, a constant strength of the bone implant may be ensured. In an alternative embodiment it may be of advantage if the base body has irregular thickness. Thus, irregularities of the osseous structure may advantageously be reconstructed or different strength requirements may be met.

It is also expedient if, in the segments of the base body which are confined by the slots, a hole formed as a through hole is formed. Preferably, the hole is arranged centrally in the respective segments. Thus, it is, for instance, easy to make a marking for characterizing the segments. Moreover, the weight of the bone implant may thus be reduced advantageously. The material costs and the production time will thus be reduced.

It is preferred if all the holes have the same size, i.e. the same diameter. This way, similar bone plates are produced.

It is expedient if the base body comprises a pore structure, in particular micro pores and/or macro pores, which may be adjusted during production. By the pore size the ingrowing of the bone implant may be influenced in a positive manner. Moreover, the weight of the bone implant may thus be reduced advantageously.

It is further of advantage if the base body has a net structure in which individual meshes/lattices have different mesh sizes. Thus, the structure of the base body may be varied and adjusted within the base body as required.

It is also of advantage if the base body has a chalky and/or glass-like/glassy surface. Thus, the material property of the base body may be influenced in a beneficial manner.

Moreover, it is preferred if the bone implant is made up or consists of a bio-absorbable material or of a non-bio absorbable material, such as a metal. The bone implant may, for instance, be made up of α—tricalcium phosphate (α-TCP), of β-tricalcium phosphate (β-TCP), of hydroxylapatite (HA), of a mixture of β-TCP and HA, i.e. a biphasic calcium phosphate (BCP). In particular a uniform structure, i.e. substantially a structure of one material, of β-TCP or HA has proved successful. Mixtures of β-TCP and HA, for instance, in the relation of 50/50 or 75/25 or 25/75, have also turned out to be particularly suitable.

In an alternative preferred embodiment it is possible to form the bone implant of a light metal, preferably of titanium, since titanium has a particularly good tolerability in the human body.

In other words, the invention relates to a bone implant that is used for obtaining autologous bone material for augmentation and/or reconstruction. In this process, an artificial defect is produced in the cranial bone by the removal of bone, and this removed bone material is transplanted at a target region. In accordance with the invention the individually designed bone implant fills the produced defect. Due to the precisely fitting 3D bone implant and the simultaneous resorption of the bone implant the bone grafting is assisted. Surgery time is reduced since the bone implant fits precisely and a lengthy adaptation during surgery is thus omitted. At the same time the bone implant serves as a guide, i.e. as a template, for the removal of bone material, so that the defect is adapted to the shape of the bone implant. The bone implant may be formed of absorbable material or of non-absorbable material. In particular, the segments formed by the slots which correspond to the shape of the removed bone material may be adapted in advance to the regions to be reconstructed at the target region.

BRIEF DESCRIPTION OF THE DRAWINGS

The invention will be explained in the following by means of drawings.

The Figures are merely of schematic nature and serve exclusively the understanding of the invention. The same elements are provided with the same reference numbers.

DETAILED DESCRIPTION

Figure 1:
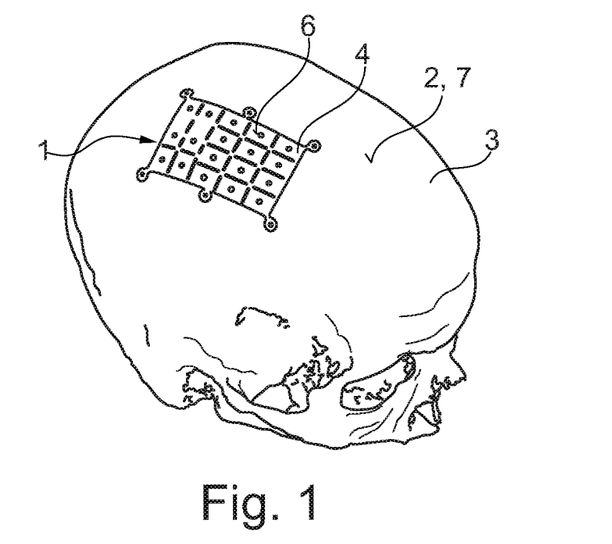
FIG. 1 is a perspective view of a bone implant in accordance with the invention which is attached to a cranial bone.

FIG. 1 shows a bone implant 1 in accordance with the invention for attaching to a surface 2 of a human cranial bone 3. The bone implant 1 comprises a plate-like base body 4. A lower side 5 of the base body 4 is a flat side and/or face of the base body 4 which faces the cranial bone 3 in the state attached to the cranial bone 3 and rests on the surface 2 of the cranial bone 3. An upper side 6 of the base body 4 is a flat side and/or face of the base body 4 which faces away from the cranial bone 3 in the state attached to the cranial bone 3. The upper side 6 is opposite to the lower side 5.

The lower side 5 corresponds substantially, for instance, with respect to its curvature, to a deformation-free or defect-free outer contour 7 of the cranial bone 3. Also the upper side 6 corresponds substantially, for instance, with respect to its curvature, to a deformation-free or defect-free outer contour 7 of the cranial bone 3. The bone implant 1 thus corresponds to a surficial bone layer and/or bone plate in the cranial bone 3 before bone material has been removed from the cranial bone 3. This means thus that the bone implant 1 fits flush, i.e. without a step, in the cranial bone 3 when inserted in the cranial bone 3 instead of bone material.

The outer dimensions of the base body 4 are chosen such that the base body 4 covers a deformation region 8 (cf. FIGS. 10 to 12) in the cranial bone 3. A deformation region 8 is a region in the cranial bone 3 in which a depression and/or recess, for instance in the manner of a blind hole, is made/inserted/formed, so that the surface 2 is deepened and/or lowered relative to a deformation-free region, for instance, to a surface region adjacent the deformation region 8. The depression is an artificially produced defect in the cranial bone 3 and is produced by the removal of bone material of the cranial bone 3. By the inserting of the bone implant 1 the deformation region is closed and/or covered, so that the bone implant 1 transits into the cranial bone 3 and the natural, i.e. original outer contour 7 of the cranial bone 3 is restored.

In the base body 4 at least one slot 9 is provided which is dimensioned such that it guides a tool 10 (cf. FIG. 6) for bone marking and/or bone processing which is inserted in the slot 9 in use during bone removal. The base body 4 thus serves, on the one hand, as an implant for covering and/or closing the artificially produced defect and, on the other hand, as a tool guiding device and/or tool guide for guiding tools during the removal of bone material from the cranial bone 3, i.e. during the production of the artificial defect, so that the geometry of the defect corresponds to the shape of the bone implant 1.

Figure 2:
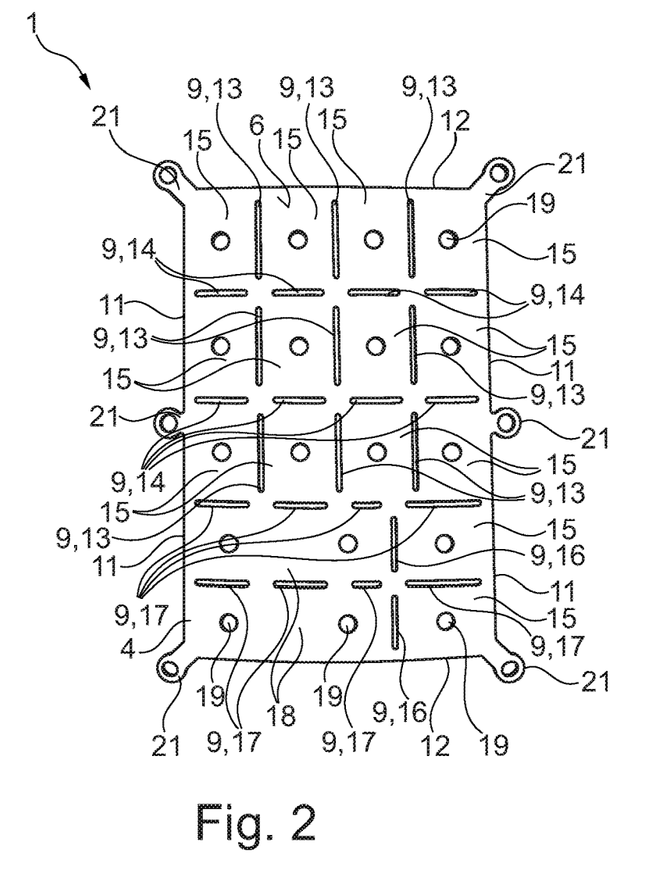
FIG. 2 is a perspective view of the bone implant on an upper side of the bone implant.
Figure 3:
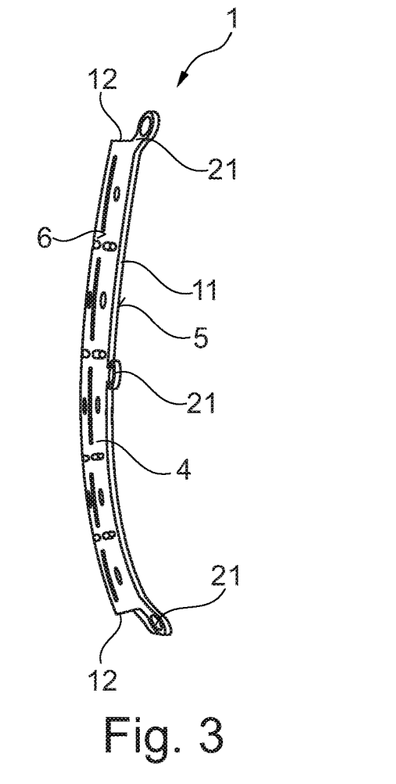
FIG. 3 is a perspective side view of the bone implant.
Figure 4:
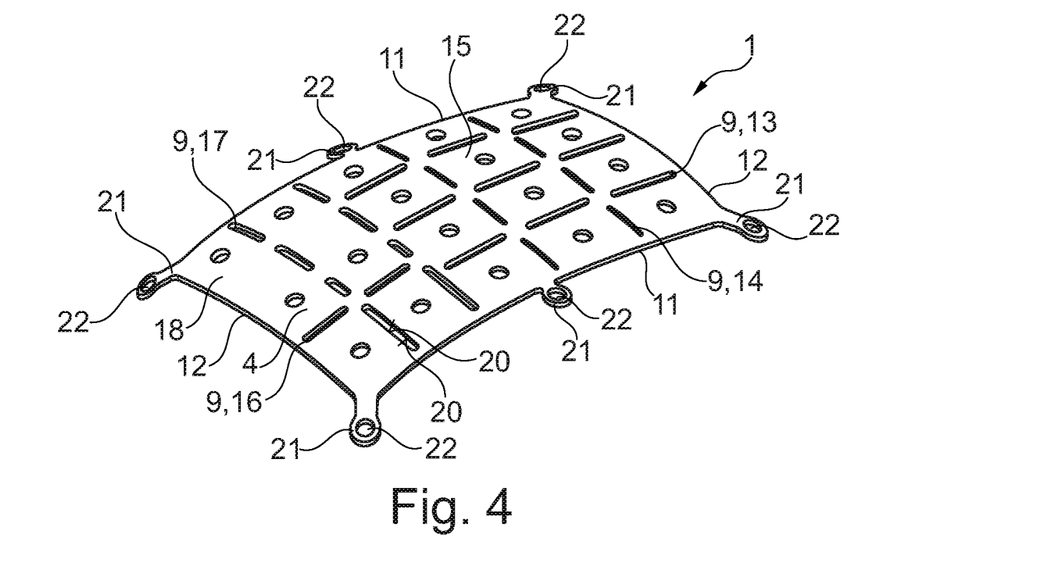
FIG. 4 is a perspective view of the bone implant which is rotated with respect to FIGS. 2 and 3.

FIGS. 2 to 4 show different perspective views of the bone implant 1. The base body 4 comprises a rectangular shape and/or outer contour and is confined by two first lateral edges 11 and/or lateral faces and two second lateral edges 12 and/or lateral faces which are shorter than the first lateral edges 11. In the base body 4 a plurality of slots 9 are provided which penetrate the base body 4 as a through hole perpendicularly to the upper side 6 and/or to the lower side 5. The slots 9 thus enable a reaching through from the upper side 6 to the lower side 5.

In the base body 4 a plurality of first slots 13 are provided whose longitudinal axes extend in parallel to the first lateral edges 11, and a plurality of second slots 14 whose longitudinal axes extend in parallel to the second lateral axes 12. The first slots 13 are longer in the longitudinal direction than the second slots 14. The first slots 13 are arranged orthogonally to the second slots 14, so that a plurality of rectangular segments 15 are formed by the slots 9 and the lateral edges 11, 12. In the illustrated embodiment every three of the first slots 13 are arranged to be flush with each other and every four of the second slots 14 are arranged to be flush with each other, so that twelve segments 15 of equal size are formed. The flush first and second slots 13, 14 are interrupted and/or separated from each other by material of the base body 4.

In the base body 4 a plurality of third slots 16 are provided whose longitudinal axes extend in parallel to the first lateral edges 11 and a plurality of fourth slots 17 whose longitudinal axes extend in parallel to the second lateral edges 12. The third slots 16 are arranged to be flush with each other and are substantially as long in the longitudinal direction as the second slots 14. In the illustrated embodiment the fourth slots 17 have a different length in the longitudinal direction and every four of the fourth slots 17 are arranged to be flush with each other, i.e. their longitudinal axes are arranged on a straight line. The third and fourth slots 16, 17 confine two segments 15 and two second segments 18 which have a larger area than the segments 15. In the segments 15 a respective hole 19 formed as a through hole and penetrating the base body 4 perpendicularly to the upper side 6 is arranged centrally. In the segments 18 two respective holes 19 are arranged. The first, second, third and fourth slots 13, 14, 16, 17 form a checkered pattern on the base body 4.

Slot rims 20 forming the lateral faces of the slots 9, as well as the first and second lateral edges 11, 12 are designed to be inclined to a plane which is perpendicular to the upper side 6 or the lower side 5. The lateral edges 11, 12 are inclined inwardly to the lower side 5, i.e. to the middle of the base body 4. The slot rims 20 are inclined to the lower side 5 to the middle of the segments 15, 18. The slots 9 are thus narrower at the upper side than at the lower side 5. The angle of inclination between a plane which is perpendicular to the upper side 6 or the lower side 5 and the slot rims 20 and/or the lateral edges 11, 12 lies between 30° and 60°.

Especially FIG. 3 reveals that the base body 4 of the bone implant 1 is concavely curved. The curvature of the base body 4 is not regular since the curvature is adapted to the cranial bone 3. The base body 4 has a constant thickness.

A plurality of fastening lugs 21 project outwardly from the base body 4 of the bone implant 1. The fastening lugs 21 are of plate-shaped design and resume a curvature of the base body 4, so that they transition seamlessly into the base body 4. The fastening lugs 21 are shaped like ears and comprise a fastening hole 22 formed as a through hole which penetrates the fastening lugs 21 perpendicularly. The fastening lugs 21 have a constant thickness which corresponds to the thickness of the base body 4. The base body 4 and the fastening lugs 21 are formed integrally.

Figure 5:
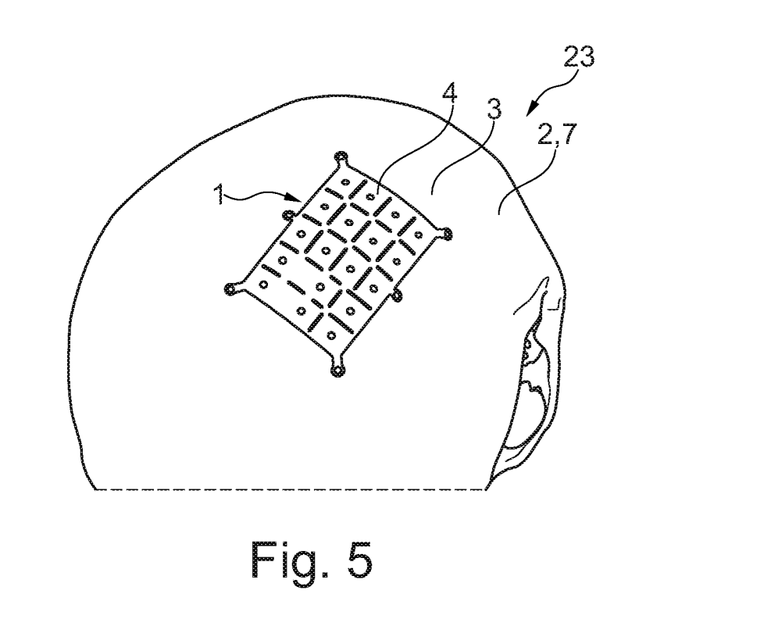
FIGS. 5 to 14 are perspective views of individual steps during the use of the bone implant in accordance with the invention.

FIG. 5 illustrates a first step 23 during the use of the bone implant 1 in which the lower side 5 of the base body 4 is placed upon the outer contour 7 of the cranial bone 3 and is positioned at the intended position at which the deformation region 8 is to be produced.

Figure 6:
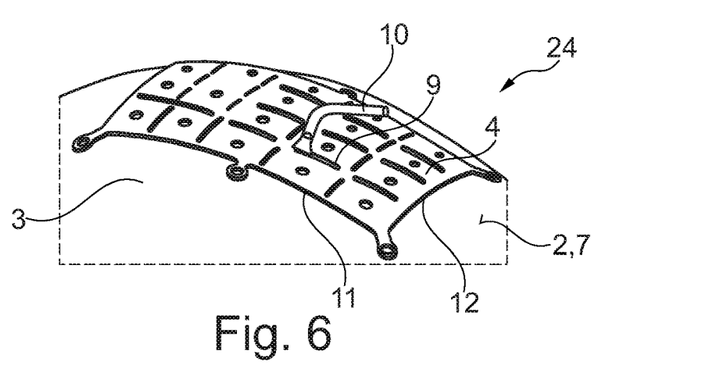
Figure 7:
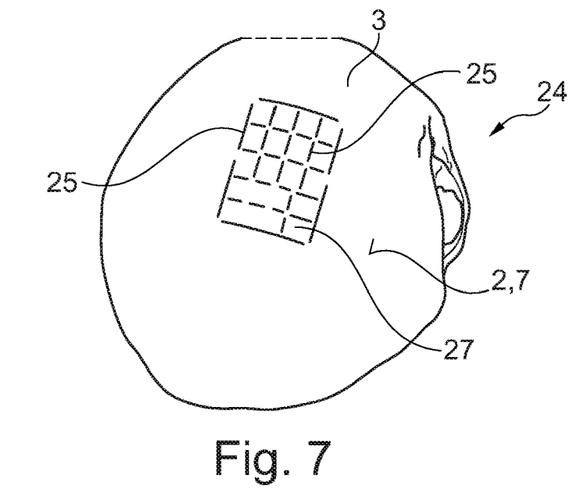

FIGS. 6 and 7 illustrate a second step 24 in which the tool 10 for bone marking and bone processing is used. The tool 10 is inserted in the slots 9 and guided by the slot rims 20. Thus, marking lines and/or sectioning lines which remove bone material are made/inserted in the cranial bone 3. The tool 10 is also guided along the first and second lateral edges 11, 12 of the base body 4. FIG. 7 shows the result of the use of the tool which illustrates checkered marking and/or sectioning lines 25 on the surface 2 of the cranial bone 3.

Figure 8:
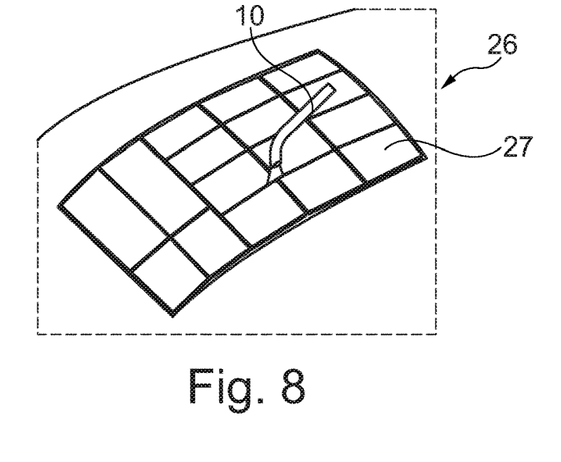
Figure 9:
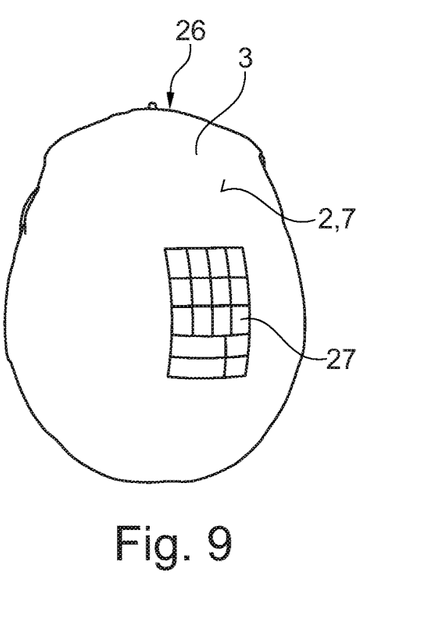

FIGS. 8 and 9 illustrate a third step 26 in which flush marking and/or sectioning lines 25 are connected with each other by the tool 10 so as to completely surround the cranial segments 27 corresponding to the segments 15, 18. The cranial segments 27 correspond to bone plates intended to be removed from the cranial bone 3.

Figure 10:
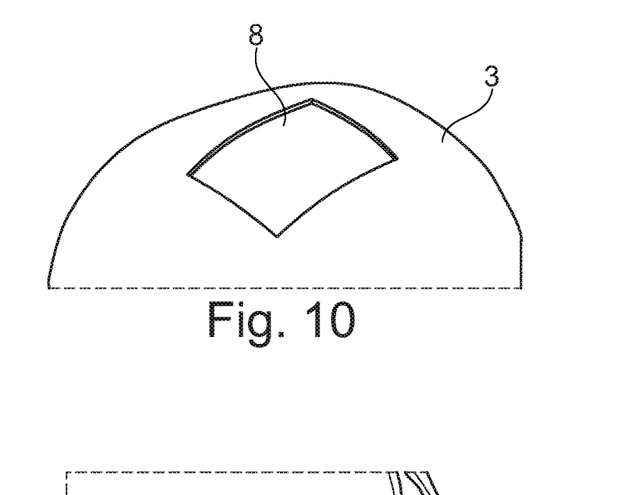

FIG. 10 illustrates the cranial bone 3 with the bone material of the cranial segments 27 removed. Thus, the deformation region 8 is formed whose shape corresponds to the outer dimensions of the base body 4. The depth of the deformation region 8 is larger than the thickness of the base body 4.

Figure 11:
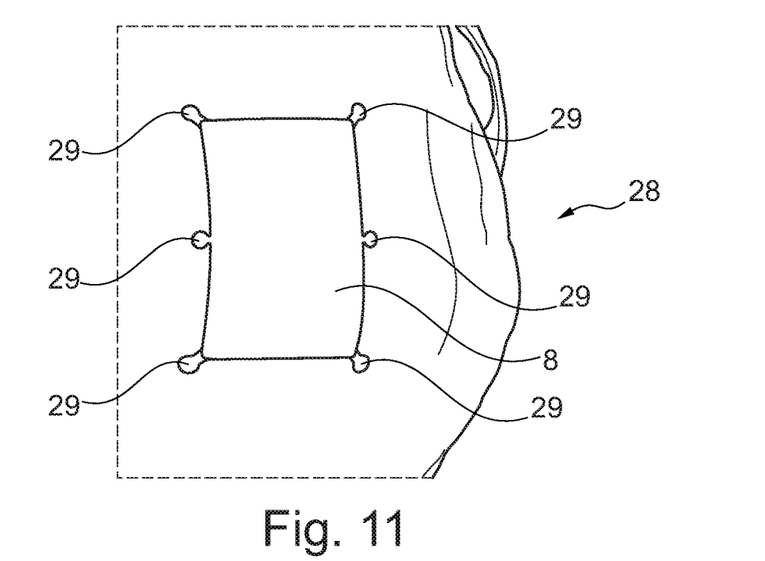
Figure 12:
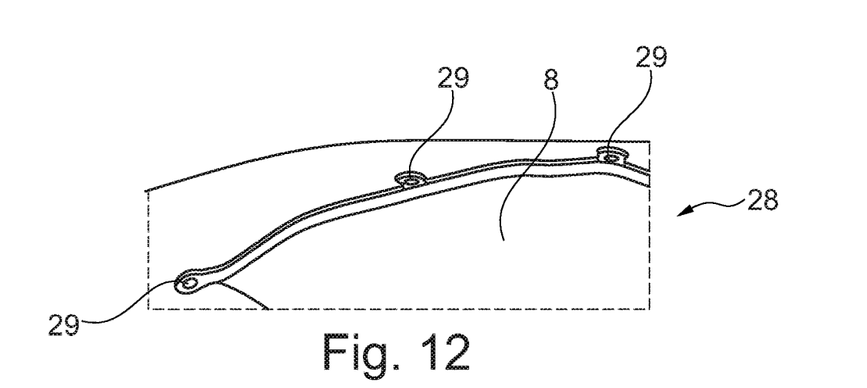

FIGS. 11 and 12 illustrate a fourth step 28 in which sinks 29 are produced in the cranial bone 3 whose depth corresponds to the thickness of the base body 4. The sinks 29 correspond in their shape to the fastening lugs 21.

Figure 13:
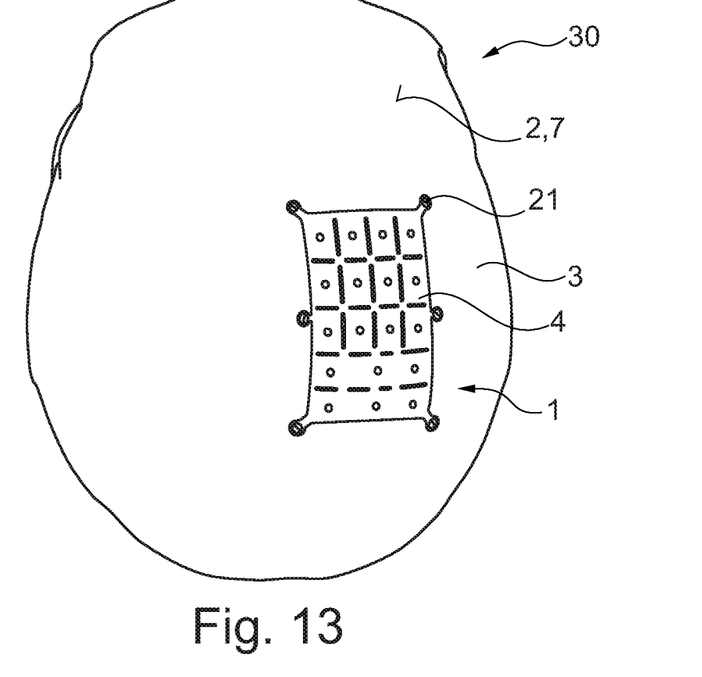
Figure 14:
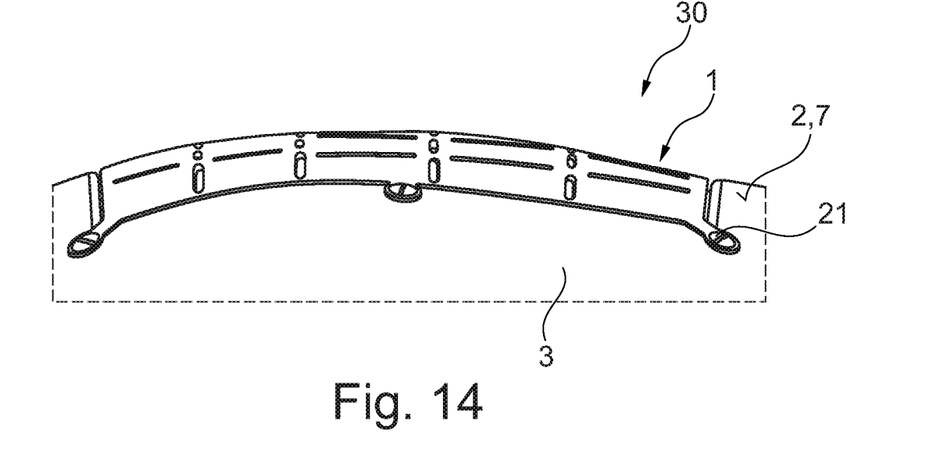

FIGS. 13 and 14 illustrate a fifth step 30 in which the base body 4 of the bone implant 1 is placed upon the deformation region 8 and the fastening lugs 21 are inserted into the sinks 29. Thus, the deformation region 8 is completely closed by the bone implant 1. The upper side 6 of the base body 4 transitions seamlessly into the outer contour 7 of the cranial bone 3, so that a flush surface 2 of the cranial bone 3 is completed. The bone implant 1 may be fastened with screws or merely be placed into the sinks 29.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

LIST OF REFERENCE SIGNS 1 bone implant
2 surface
3 cranial bone
4 base body
5 lower side
6 upper side
7 cranial outer contour
8 deformation region
9 slot
10 tool
11 first lateral edge
12 second lateral edge
13 first slot
14 second slot
15 segment
16 third slot
17 fourth slot
18 segment
19 hole
20 slot rim
21 fastening lug
22 fastening hole
23 first step
24 second step
25 marking/sectioning line
26 third step
27 cranial segments
28 fourth step
29 sink
30 fifth step

We claim:

1. A bone implant for attaching to a surface of a bone, comprising:
   a base body whose lower side and/or upper side are/is configured to correspond substantially to a deformation-free bone outer contour,
   the base body having outer dimensions that are chosen such that the base body is configured to cover a specifically introduced deformation region for obtaining autologous bone material completely,
   the base body having at least one slot which is dimensioned such that it guides a bone marking and/or bone processing tool inserted in the slot in use,
   the base body having an outer contour which is designed as a guiding face for the bone marking and/or bone processing tool, and
   the at least one slot and the outer contour each having straight side faces being inclined inwardly from the upper side to the lower side of the base body.

2. The bone implant according to claim 1, wherein the slot is designed as an elongate through hole enabling the bone marking and/or bone processing tool to reach from the upper side of the base body through material of the base body and beyond the lower side of the base body.

3. The bone implant according to claim 1, wherein a plurality of slots are provided, at least two of said plurality of slots being arranged orthogonally to each other.

4. The bone implant according to claim 1, wherein the lower side of the base body is concavely shaped.

5. The bone implant according to claim 1, wherein a plurality of slots are separated in alignment with each other by material of the base body.

6. The bone implant according to claim 1, wherein the bone implant comprises fastening lugs projecting outwardly from the base body.

7. The bone implant according to claim 1, wherein the base body has a constant thickness.

8. The bone implant according to claim 1, wherein the bone implant is made up or consists of a bio absorbable material or of a non-bio absorbable material and/or that the bone implant comprises a doping with an antimicrobacterial property.

9. The bone implant according to claim 1, wherein the side faces of the at least one slot and or the side faces of the outer contour are inclined between 30 and 60°.

* * * * *